United States Patent [19]

Imahori et al.

[11] Patent Number: 4,572,894

[45] Date of Patent: Feb. 25, 1986

[54] PROCESS FOR SYNTHESIZING PEPTIDES OR PEPTIDE DERIVATIVES

[75] Inventors: Kazutomo Imahori, No. 2-25-23, Kakinokisaka, Meguro-ku, Tokyo; Hiroshi Nakajima, Kyoto; Tatsuo Iwasaki, Kyoto; Isao Tomioka, Kyoto; Keiichi Yamamoto, Kyoto, all of Japan

[73] Assignees: Kazutomo Imahori; Rikagaku Kenkyusho; Unitika Ltd., all of Japan

[21] Appl. No.: 461,307

[22] Filed: Jan. 26, 1983

[30] Foreign Application Priority Data

Jan. 26, 1982 [JP] Japan ................. 57-10336
May 27, 1982 [JP] Japan ................. 57-90425
May 27, 1982 [JP] Japan ................. 57-90426
Dec. 9, 1982 [JP] Japan ................. 57-216206

[51] Int. Cl.$^4$ .................. C12P 21/00; C12P 21/02; C12N 9/00
[52] U.S. Cl. ......................... 435/68; 435/70; 435/183
[58] Field of Search ............. 435/68, 70, 71, 183, 435/232, 212

[56] References Cited

U.S. PATENT DOCUMENTS 3,544,426 12/1970 Snellman ........................ 435/70

OTHER PUBLICATIONS

Lehninger, Albert L., *Biochemistry,* Worth Publishers, Inc., Chapter 30, pp. 689–694, ©1970.
Woodward, et al., Chapter 67c in *Methods in Enzymology,* Academic Press, 1974, pp. 740–746.

*Primary Examiner*—Alvin E. Tanenholtz
*Assistant Examiner*—Jayne A. Huleatt
*Attorney, Agent, or Firm*—Sughrue, Mion, Zinn, Macpeak, and Seas

[57] ABSTRACT

A process for synthesizing peptides or peptide derivatives is disclosed. The process involves using aminoacyl-tRNA synthetase as a condensing agent when synthesizing peptides or peptide derivatives from amino acids. According to the process, peptides or peptide derivatives which are useful as various hormones such as bradykinin having antihypertensive activity or somatostatin having an internal or external secretion controlling function and other biologically active substances such as antibiotic peptides or seasoning peptides can be produced at a moderate price without using protective groups.

23 Claims, No Drawings

PROCESS FOR SYNTHESIZING PEPTIDES OR PEPTIDE DERIVATIVES

FIELD OF THE INVENTION

The present invention relates to a novel process for synthesizing peptides or peptide derivatives.

BACKGROUND OF THE INVENTION

In recent years, the various physiological activities have become known as have the importance of peptides as medical supplies for medical treatment, diagnosis or other uses and as seasoning agents. Accordingly, there has been a great deal of development of the processes for synthesizing peptides. Chief processes for synthesizing peptides which are now known can be classified into chemical synthesis processes and enzymatic synthesis processes as described in *Pharmacia Review*, No. 3, pages 27-47 (1980). The chemical synthesis processes include condensing amino acids one by one by an azide process, a mixed acid anhydride process, an active ester process or a carbodiimide process and a process which comprises condensing with fragments. However, in any of these chemical synthesis processes, there are various problems. More specifically, racemization and side reactions are easily caused and the reaction time is long and the end amino group must be previously protected with a protective group before the reaction. With respect to the fragment condensation process, there is a serious fault in that racemization is particularly easily caused.

In order to avoid the occurrence of racemization as much as possible, an enzymatic synthesis process using protease has been proposed in U.S. Pat. No. 4,119,493. In this process, however, complexity of operation is still not improved, because the reaction time is long and the end amino group must be protected. Further, the enzymatic synthesis process using protease has a serious fault in that the desired peptide cannot be obtained frequently, because the formed peptide is decomposed during synthesis thereof. This occurs because the enzyme used has an inherent activity which involves decomposing peptides. Particularly, when applying this process to the synthesis of and oligopeptide, there is a serious fault in that undesired peptides are obtained wherein a part of the amino acids are lacking in *Journal of Biological Chemistry*, Vol. 256, page 1301 (1981). A known process for synthesizing peptides by enzymatic synthesis involves using a special enzyme which synthesizes only one peptide having a specified amino acid arrangement, in addition to the protease process. Examples of such enzymes include glutathione synthesizing enzyme which synthesizes tripeptide having an arrangement of glutamic acid/cystein/glycine as described in Japanese Patent Application (OPI) No. 122793/79 (The term "OPI" as used herein refers to a "published unexamined Japanese patent application".) and gramicidin S synthesizing enzymes which synthesize gramicidin S of decapeptide as described in *Gendai Kagaku*, December 1974, page 12. However, these enzymes are special ones and a desired suitable peptide can not be synthesized because only one limited kind of peptide is synthesized by them. Therefore, under existing circumstances, this process can not be used as a general process for synthesizing peptides.

SUMMARY OF THE INVENTION

An object of the present invention is to provide a novel process for synthesizing a peptide or derivatives thereof which can be generally utilized, capable of eliminating the racemization and side reactions.

Another object of the present invention is to provide a novel process for synthesizing a peptide or derivatives thereof which can be generally utilized, without the need for protecting the end amino group which causes the occurrence of the complexity of operation and deteriorates economic efficiency.

As a result of diligent research to attain the above described, the present inventors have found that aminoacyl-tRNA synthetase, which is an enzyme that function in bonding amino acid to tRNA, a nucleic acid, and has not been known to function in the formation of a peptide bond is surprisingly capable of synthesizing peptides. The above described object can be attained by using such an enzyme as a condensing agent.

The present invention involves a process for synthesizing peptides or peptide derivatives which comprises using aminoacyl-tRNA synthetase as a condensing agent when synthesizing peptides or peptide derivatives from amino acids.

According to the present invention, useful peptides or peptide derivatives can be produced at a moderate price without using protective groups.

Further, the useful peptides and peptide derivatives can be effectively produced without the occurrences of racemization and side reactions.

DETAILED DESCRIPTION OF THE INVENTION

A characteristic of the present invention is the ability to synthesize peptides or peptide derivatives in high yield without protecting amino groups by using aminoacyl-tRNA synthetase as a condensing agent in the process. The peptides are synthesized by an enzymatic process.

Aminoacyl-tRNA synthetase used in the present invention belongs to enzyme classification 6.1.1, which is an enzyme having a catalytic function for the following reaction:

Amino acid+ATP+tRNA→aminoacyl-tRNA+AMP-+pyrophosphoric acid

Examples of it include those obtained from animal tissue such as that of rabbits, horses, cattle, rats, chickens or snakes, etc., those obtained from vegetable tissue such as rice plants, potatoes or tomatoes, etc. and those obtained from microbes such as molds, yeasts, fungi, bacteria or Actinomycetes, etc. or seaweeds. Particularly, those obtained from microbes are preferred, because treatment of them is easily carried out. Futhermore, aminoacyl-tRNA synthetase obtained from thermophilic bacteria such as *Bacillus stearothermophilus, Thermus thermophilus, Thermus flavus, Clostridium thermoaceticum* or *Thermus aquaticus* are most preferred with respect to the stability of enzymes.

These various kinds of aminoacyl-tRNA synthetase can be obtained by crushing the above described tissue or cells with a homogenizer or a cell mill and purifying by a conventional enzyme purification process such as chromatography e.g., DEAE-cellulose column chromatography or hydroxy apatite column chromatography, etc. or fractional precipitation by ammonium sulfate, etc. as described in, for example *Biochemistry*, Vol. 13, page 2307 (1974). Useful aminoacyl-tRNA synthetases include those with specificity to various α-amino acids. Examples of useful enzymes include tyrosyl-tRNA synthetase with specificity to tyrosine, leucyl-tRNA synthetase with specificity to leucine and valyl-tRNA synthetase with specificity to valine. In addition, there are isoleucyl-tRNA synthetase, phenyl-alanyl-tRNA synthetase, alanyl-tRNA synthetase, glutamyl-tRNA synthetase, aspartyl-tRNA synthetase, methionyl-tRNA synthetase, histidyl-tRNA synthetase, lysyl-tRNA synthetase, threonyl-tRNA synthetase and seryl-tRNA synthetase, etc.

In the present invention, the aminoacyl-tRNA synthetase may be used as a crude enzyme extract solution containing aminoacyl-tRNA synthetase which is obtained by crushing the above described tissue or cells by a homogenizer or a cell mill, etc. and treating the resulting crude extract solution with a cation exchange resin having phosphoric acid groups.

In order to carry out the treatment with the cation exchange resin having phosphoric acid groups, the above described crude extract solution may be added to the cation exchange resin having phosphoric acid groups which are equilibrated with a buffer solution having a pH of 3 to 12 and, preferably, 6 to 9 and, most preferably, 7 to 8 and a concentration of 1 mM to 1M and, preferably 20 mM to 100 mM (batch process). Alternatively, the crude extract solution may be allowed to pass through a column packed with the above described resin (column process).

In these cases, the treatment is carried out at a temperature which maintains the activity of the aminoacyl-tRNA synthetase. It is generally preferred to carry out the treatment at a temperature of 0° C. to 70° C. and, more preferably, 0° C. to 30° C. Further, as the buffer solution used, any solution may be added if it dissolves the aminoacyl-tRNA synthetase resulting in the desired pH. Preferred examples of such solutions include a tris-hydrochloric acid buffer solution, a HEPES buffer solution, a triethanolamine buffer solution, an imidazole buffer solution and a phosphoric acid buffer solution, etc, more preferably phosphoric acid buffer solution.

In order to prevent deactivation of the enzyme, sulfhydrylating agents such as mercaptoethanol or dithiothreitol, etc., protease inhibitors such as phenylmethylsulfonyl fluoride, etc., and chelating agents such as sodium ethylenediaminetetraacetate, etc. may be added to the buffer solution.

In order to carry out the treatment with the above described batch process, the crude extract solution is added to a cation exchange resin having phosphoric acid groups which are equilibrated with the above described buffer solution, followed by stirring for 5 minutes or more and, preferably, 30 minutes or more. After being allowed to stand for a while, the enzyme absorbed is eluted with the same buffer solution, the above described solution having a different pH, a buffer solution having a different concentration or a buffer solution containing other salts. Accordingly, a crude enzyme solution containing aminoacyl-tRNA synthetase can be obtained. Further, in order to carry out the treatment with the column process, for example, an absorption-desorption operation for the desired enzyme is carried out in a column, the principle of which is the same as that of the batch process. The treatment is preferably carried out as rapidly as possible, and it is preferably carried out at a velocity of 1 cm.h$^{-1}$ or more in the column. Further, considering separation ability, it is more preferred if the velocity in the column is not more than 60 cm.h$^{-1}$. Salts used for elution in the batch process and the column process, include any substance which completely dissociates, but it is particularly preferred to use a salt wherein the component becoming a pair ion of the ion exchange group is the same of that in the buffer solution used.

The resulting crude enzyme solution containing the aminoacyl-tRNA synthetase may be used as it is, or it may be used in a solid state prepared by freeze drying.

The resulting crude enzyme solution containing aminoacyl-tRNA synthetase may be subjected to DEAE resin treatment so that it can be used for the synthesis of peptides.

The cation exchange resin having phosphoric acid groups used in the present invention may be any material wherein the exchange group is a phosphoric acid group. Particularly, it is preferred to use cellulose phosphate resin using cellulose as a base material (for example, those produced by Whatman Co., Bio-Rád Co. and Serva Co.) because a crude enzyme solution containing a desired aminoacyl-tRNA synthetase can be prepared rapidly in a high yield, whereby peptides or peptide derivatives can be synthesized in a high yield by using such a crude enzyme solution.

In the following, the process for synthesizing peptides or peptide derivatives from amino acids according to the present invention is illustrated in detail. According to the present invention, peptides or peptide derivatives can be synthesized by reacting an amino acid with an amino acid derivative derived from amino acids with the reaction being carried out in the presence of aminoacyl-tRNA synthetase. Further, according to the present invention, peptides or peptide derivatives can be synthesized by previously reacting an amino acid with aminoacyl-tRNA synthetase and reacting the resulting reaction mixture with an amino acid derivative. Amino acids suitably used for previously reacting with aminoacyl-tRNA synthetase include tyrosine, alanine, leucine, isoleucine, phenylalanine, methionine, lysine, serine, valine, asparagine, aspartic acid, glycine, glutamine, glutamic acid, cysteine, threonine, tryptophane, histidine or proline, etc., which may be in the L-compound and D-compound form. Further, useful amino acid derivatives include esters, thioesters, amides and hydroxamides, etc. of various amino acids, for example, α-amino acids such as glycine, alanine, leucine, isoleucine, phenylalanine, glutamic acid, glutamine, norleucine, cysteine, tyrosine, alginine, valine, lysine, histidine, aspartic acid, asparagine, methionine, tryptophane, arginine or threonine, etc., β-amino acids such as β-alanine or β-aminoisobutyric acid, etc., nitrogen containing γ-amino acids such as creatine, etc., γ-amino acids such as piperidic acid, etc., and ε-amino acids such as ε-aminocapronic acid, etc. However, the amino acid derivatives are not limited to the above described compounds, if they have a free amino group. Various esters can be used such as simple hydrocarbon esters including methyl, ethyl, propyl, cyclohexyl, phenyl or benzyl ester as well as esters prepared by esterifying the 3'-OH of tRNA with the above described amino acids. Further, useful amides include free amides as well as oligopeptides and polypeptides wherein amide bonds are formed with different kinds or the same kinds of amino acids. It is also possible to use esters, thioesters, hydroxamides and ethers of the above described oligopeptides and polypeptides. Further, the above described amino acid derivatives may be used in the form of an aqueous solution or in a solid state.

The reaction mixture is prepared by mixing an amino acid with aminoacyl-tRNA synthetase in a buffer solution having a pH of 5 to 11, preferably, 6 to 10 and, more preferably, 7 to 10 in the presence of adenosine triphosphate or deoxyadenosine triphosphate. In this case, the reaction is preferably carried out at a temperature of, generally, 0° C. to 70° C. and, more preferably 0° C. to 30° C. in order to maintain the activity of the enzyme. The reaction may be carried out at atmospheric pressure. Useful buffer solutions include any solution which dissolves the amino acid, adenosine triphosphate, deoxyadenosine triphosphate and aminoacyl-tRNA synthetase so as to have a desired pH. Examples of the buffer solution include a tris-hyrochloric acid buffer solution, a HEPES buffer solution, a triethanolamine buffer solution, a maleate buffer solution and a phosphoric acid buffer solution, etc. The pH value and concentration of the preferred buffer solution are preferably 7 to 8 and 20 mM to 100 mM, respectively. Further, mixed media prepared by adding hydrophilic organic solvents to these buffer solutions can be used, if they satisfy the above described requirements. Examples of such hydrophilic organic solvents include ethers such as dioxane or tetrahydrofuran, etc., dimethylsulfoxide, dimethylformamide, acetonitrile and acetone, etc.

The concentration of the hydrophilic organic solvent in the whole reacting solution is in a range of 0.5 to 85%, preferably 5 to 60%, and more preferably 10 to 50%. Further, since the hydrophilic organic solvent needs merely be present when carrying out the peptization reaction, it may be added at any time. When the hydrophilic organic solvent is used, it is possible to reduce the concentration of the amino acid derivative as a raw material. Furthermore, in order to smoothly carry out the reaction and to prevent deactivation of the enzyme, divalent cations such as magnesium or manganese, etc., sulfhydrylating agents such as mercaptoethanol or dithiothreitol, etc. and pyrophosphatase may be added alone or as a mixture of them to the reaction system. The preferred concentration of each additive is 0.01 mM to 500 mM of divalent cation, 0.001 mM to 100 mM of sulfhydrylating agent and 0.001 units/ml to 100 units/ml of pyrophosphatase, respectively. The optimum concentration is 0.1 mM to 10 mM of divalent cation, 0.01 mM to 1 mM of sulfhydrylating agent and 1 unit/ml to 10 units/ml of pyrophosphatase, respectively.

The amounts of the amino acid, aminoacyl-tRNA synthetase and adenosine triphosphate or deoxyadenosine triphosphate used are not particularly limited, but it is preferred to carry out the reaction in a molar ratio of amino acid to aminoacyl-tRNA synthetase of 10:1 to 1:10 and a molar ratio of amino acid to adenosine triphosphate or deoxyadenosine triphosphate of 1:10 to 1:100, in order to obtain a practical yield. When the reaction is carried out under the above described condition, it smoothly proceeds and concludes within a few seconds to 30 minutes.

The resulting reaction mixture is then allowed to react with an amino acid derivative by blending, by which the desired peptide or peptide derivative can be obtained (this stage is called, hereinafter, "peptization"). In this case, the reaction mixture may be used as it is for the peptization reaction. However, it also may be used after the adenosine triphosphate, adenosine monophosphate or pyrophosphoric acid, etc. present after the reaction is removed by gel chromatography with G-25 (produced by Pharmacia Co.) or G-75 (produced by Pharmacia Co.), etc. Further, the peptization reaction is preferably carried out at a temperature of 0° C. to 70° C. In order to prevent deactivation of the enzyme and obtain a proper reaction rate, it is preferred to carry out the reaction at 10° C. to 50° C., more preferably at 20° C. to 40° C. Further, the pH during the reaction is in the range of 5 to 11, preferably 6 to 11, and more preferably 7 to 9.

The reaction mixture and an amino acid derivative are blended in a ratio by volume of, for example, 1:0.1 to 1:100. Further, the concentration of the amino acid derivative used in this case is in a range of 10 mM to 10M, and preferably 100 mM to 2M, but a lower concentration may be used.

Particularly, in the present invention, an amino acid and an amino acid derivative are reacted in the presence of aminoacyl-tRNA synthetase by previously obtaining a mixture of the amino acid and the amino acid derivative and blending the resulting mixture with aminoacyl-tRNA synthetase or by previously obtaining a mixture of amino acid derivative and aminoacyl-tRNA synthetase and blending the resulting mixture with an amino acid. When such a reaction is carried out, peptides or peptide derivatives are obtained in a high yield, even if the concentration of expensive aminoacyl-tRNA synthetase is very low. In order to synthesize peptides or peptide derivatives by this process, an amino acid and an amino acid derivative are previously blended in the above described buffer solution in the presence of adenosine triphosphate or deoxyadenosine triphosphate, or an amino acid derivative and aminoacyl-tRNA synthetase are previously blended in the above described buffer solution in the presence of adenosine triphosphate or deoxyadenosine triphosphate. In this case, the above described sulfhydrylating agent and pyrophosphatase may be added alone or as a mixture in order to smoothly carry out the subsequent reaction and to prevent deactivation of enzyme. The amounts of these components are as described above, but the amount of aminoacyl-tRNA synthetase is about 1/1,000 to 1/10,000 of the above described amount.

The resulting mixture of an amino acid and an amino acid derivative is then blended with aminoacyl-tRNA synthetase or the resulting mixture of an amino acid derivative and aminoacyl-tRNA synthetase is blended with an amino acid to react the amino acid with the amino acid derivative in the presence of the aminoacyl-tRNA synthetase. The pH and the temperature during this reaction are the same as those in case of the above described peptization.

Peptization under the above described condition concludes within a few seconds to a few days, by which the desired peptides or peptide derivatives can be obtained.

The peptide derivatives obtained by the present invention are useful as various hormones such as bradykinin having antihypertensive activity or somatostatin having an internal or external secretion controlling function and other biologically active substances such as antibiotic peptides or seasoning peptides, etc.

According to the present invention, the above described useful peptides or peptide derivatives can be produced at a moderate price without using protective groups.

Further, the useful peptides and peptide derivatives can be effectively produced without causing the occurrences of racemization and side reactions.

In the following, the present invention is illustrated in greater detail by examples.

REFERENCE EXAMPLE 1

After 500 kg of *Bacillus stearothermophilus* NCA 1503 was crushed by a Dinomill (produced by Shinmaru Enterprises Co.), the resulting crude extract solution was purified by chromatography with DEAE-cellulose (produced by Whatman Co.), chromatography with hydroxyapatite (produced by Seikagaku Kogyo Co.), ammonium sulfate fractionation, chromatography with Gel ACA 34 (produced by LKB Co.) and chromatography with DEAE cellulose to obtain 8.3 g of tyrosyl-tRNA synthetase with specificity to tyrosine.

REFERENCE EXAMPLE 2

After 1000 kg of *Saccharomyces cerevisiae* α S288C was crushed by a Dynomill, the resulting crude extract solution was subjected to ammonium sulfate fractionation, chromatography with DEAE-cellulose, chromatography with cellulose phosphate (produced by Whatman Co.), chromatography with DEAE-Sephacel (produced by Pharmacia Co.), chromatography with Ultrogel ACA34 and chromatography with CM-cellulose (produced by Whatman Co.) to obtain 3.2 g of leucyl-tRNA synthetase with specificity to leucine.

REFERENCE EXAMPLE 3

After 1000 kg of rabbit liver was crushed by a Waring blender, it was centrifugally processed (15,000 g). The supernatant solution was subjected to ultracentrifugation (105,000 g) to obtain a soluble protein fraction. It was then subjected to ammonium sulfate fractionation, gel chromatography with Sephadex G-200 (produced by Pharmacia Co.), chromatography with DEAE-Sephacel and chromatography with hydroxyapatite to obtain 4.5 g of methionyl-tRNA synthetase.

REFERENCE EXAMPLE 4

1.5 g of aspartyl-tRNA synthetase with specificity to aspartic acid was obtained from 150 kg of *Escherichia coli* K-12 by the same column operation as in Reference Example 1.

REFERENCE EXAMPLE 5

1.1 g of arginyl-tRNA synthetase having specificity to arginine was obtained from 100 kg of *Bacillus stearothermophilus* UK-788 (Deposition No. 5141 in Fermentation Research Institute) by the same column operation as in Reference Example 1.

EXAMPLE 1

0.6 g of tyrosyl-tRNA synthetase with specificity to tyrosine obtained in Reference Example 1, 0.4 g of magnesium chloride, 0.1 g of disodium adenosine triphosphate, 1 mg of L-tyrosine, 200 units of pyrophosphatase (produced by Boehringer Mannheim Co.) and 0.01 mg of dithiothreitol were dissolved in 200 ml of a 20 mM HEPES buffer solution at pH 8.0, and they were reacted at 4° C. for 15 minutes to obtain a reaction mixture, 4 g of L-phenylalanine methyl ester was added to the resulting mixture and well blended, and the mixture was allowed to stand for a day while maintaining the reaction temperature at 30° C. to carry out the reaction.

200 ml of acetone was added to the resulting reaction solution. After precipitates were filtered out, the supernatant solution was concentrated by an evaporator to about 20 ml, and it was put in a μ Bondapak $C_{18}$ column (produced by Waters Co.) and treated with an aqueous solution of acetonitrile/50 mM potassium phosphate: 85/15 having pH 7 as a developing solution to separate 0.4 mg of L-tyrosyl-L-phenylalanine methyl ester.

Elementary analysis of it ($C_{19}H_{22}N_2O_4 = 342.39$) was as follows: Calculation value (%): C: 66.65; H: 6.48; N: 8.18; Measured value (%): C: 66.55; H: 6.40; N: 8.27

EXAMPLE 2

4 g of tyrosyl-tRNA synthetase used in Example 1, 250 mg of magnesium chloride, 200 mg of disodium adenosine triphosphate, 9 mg of L-tyrosine, 200 units of pyrophosphatase (produced by Boehringer Mannheim Co.) and 0.01 mg of dithiothreitol were dissolved in 20 ml of a 10 mM HEPES buffer solution at pH 8.5. After conducting the reaction at 4° C. for 20 minutes, the reaction mixture was put in a G-75 (produced by Pharmacia Co.) column and elution was carried out with the same HEPES buffer solution as described above to collect 30 ml of the fraction of voids, and a reaction mixture was isolated. To the isolation reaction mixture, 4 g of D-leucine ethyl ester was added and well blended, and the mixture was allowed to react for 30 minutes while maintaining the reaction temperature at 20° C.

The resulting reaction solution was put in a μ Bondapak $C_{18}$ column, and separation was carried out by the same manner as in Example 1 to obtain 16 mg of L-tyrosyl-D-leucine ethyl ester.

Elementary analysis of it ($C_{17}H_{26}N_2O_4 = 322.39$) was as follows: Calculation value (%): C: 63.33; H: 8.13; N: 8.69; Measured value (%): C: 63.42; H: 8.10; N: 8.57

EXAMPLE 3

20 mg of tyrosyl-tRNA synthetase obtained from baker's yeast in the same manner as in Reference Example 1 according to the process described in *J. Biol. Chem.*, 63, 434 (1968), 20 mg of magnesium chloride, 5 mg of disodium adenosine triphosphate, 0.1 mg of D-tyrosine, 10 units of pyrophosphatase (produced by Boehringer Mannheim Co.) and 20 μl of mercaptoethanol were added to 20 ml of a 30 mM 2,5-dimethylimidazole buffer solution having pH 9. After being allowed to react similarly to Example 2, a reaction mixture was isolated similarly to Example 2. 1 g of L-leucine ethyl ester was added in a solid state to the resulting reaction mixture to react at 20° C. for 5 hours. To the resulting reaction product, 20 ml of acetone was added, and the produced precipitate was filtered out. After being concentrated to about 10 ml by an evaporator, separation was carried out by the same manner as in Example 1 to obtain 0.15 mg of D-tyrosyl-L-leucine ethyl ester.

Elementary analysis of it ($C_{17}H_{26}N_2O_4 = 322.39$) was as follows: Calculation value (%): C: 63.33; H: 8.13; N: 8.69; Measured value (%): C: 63.15; H: 8.24; N: 8.50

EXAMPLE 4

0.4 g of seryl-tRNA synthetase obtained from porcine pancreas by the same method as in Reference Example 3 according to the description of *J. Biol. Chem.* 237, 3698 (1962), 50 mg of magnesium chloride, 20 mg of disodium deoxyadenosine triphosphate, 1 mg of L-serine, 200 units of pyrophosphatase (produced by Boehringer Mannheim Co.) and 0.01 mg of dithiothreitol were reacted by the same method as in Example 2, and a reaction mixture was obtained using a G-25 column (produced by Pharmacia Co.).

The reaction mixture was blended with 4 g of β-alanylamide to react at 50° C. for 10 minutes. The resulting reaction solution was treated with a μ Bondapak $C_{18}$ column by the same method as in Example 1 to carry out separation, by which 1 mg of L-seryl-β-alanylamide was obtained.

Elementary analysis of it ($C_6H_{13}N_3O_3$=175.19) was as follows: Calculation value (%): C: 41.14; H: 7.48; N: 23.99; Measured value (%): C: 41.20; H: 7.52; N: 24.10

EXAMPLE 5

To 45 ml of a 20 mM PIPES buffer solution containing 8 g of L-phenylalanine ethyl ester having pH 7.0, 0.15 g of magnesium chloride, 0.3 g of disodium adenosine triphosphate, 10 mg of L-tyrosine, 200 units of pyrophosphatase (produced by Boehringer Mannheim Co.) and 0.01 mg of dithiothreitol were added, and the volume of the mixture was adjusted to 5 ml. While maintaining the pH of the mixture at 7.0, 0.6 mg (1/1000 of the amount in Example 1) of tyrosyl-tRNA synthetase obtained in Reference Example 1 was added thereto and well blended. The mixture was allowed to stand for one day while maintaining the reaction temperature at 30° C. to carry out the reaction.

The resulting reaction solution was put in a μ Bondapak $C_{18}$ column (produced by Waters Co.) and treated with an aqueous solution of acetonitrile/50 mM potassium phosphate: 85/15 having pH 7 as a developing solvent to separate 17 mg of L-tyrosyl-L-phenylalanine ethyl ester.

Elementary analysis of it ($C_{20}H_{24}N_2O_4$=356.42) was as follows: Calculation value (%): C: 67.39; H: 6.80; N: 7.86; Measured value (%): C: 67.18; H: 6.91; N: 7.72

EXAMPLES 6, 7 AND 8

To 45 ml of a 50 mM PIPES buffer solution containing 9.5 g of L-alginine-t-butyl ester having pH 7.5, 100 mg of magnesium chloride, 200 mg of disodium adenosine triphosphate, 9 mg of L-tyrosine, 200 units of pyrophosphatase (produced by Boehringer Mannheim Co.) and 0.01 mg of dithiothreitol were added, and the volume was adjusted to 50 ml while maintaining the pH of the mixture at 7.5. To the resulting mixture, 0.4 mg (1/10000 of the amount in Example 2) of tyrosyl-tRNA synthetase obtained in Reference Example 1 was added and well blended. The reaction was carried out for 2 hours while maintaining the pH at 7.5 and the reaction temperature at 40° C. Then the resulting reaction solution was treated by the same method as in Example 5 to separate 17.5 mg of L-tyrosyl-L-alginine-t-butyl ester.

Elementary analysis of it ($C_{19}H_{31}N_5O_4$=393.49) was as follows: Calculation value (%): C: 58.00; H: 7.94; N: 17.80; Measured value (%): C: 57.83; H: 7.90; N: 17.78

8.3 g of D-alginine ethyl ester was added instead of L-alginine-t-butyl ester, and the reaction was carried out by the same method as in Example 6 (Example 7). As the result, 16 mg of L-tyrosyl-D-alginine ethyl ester was obtained.

Further, the reaction was carried out by the same method as in Example 6 using D-tyrosine instead of L-tyrosine in Example 6 (Example 8). As the result, 17.0 mg of D-tyrosyl-L-alginine-t-butyl ester was obtained.

EXAMPLE 9

To 13 ml of a 30 mM 2,5-dimethylimidazole buffer solution containing 2 g of L-phenylalanine methyl ester having pH 7.2, 20 mg of magnesium chloride, 50 mg of disodium adenosine triphosphate, 10 units of pyrophosphatase (produced by Boehringer Mannheim Co.), 20 μl of mercaptoethanol and 3 mg of leucyl-tRNA synthetase obtained in Reference Example 2 were added, and the volume was adjusted to 15 ml while maintaining the pH of the mixture at 7.2. To the resulting mixture, 1 mg of D-leucine was added and well blended, and the reaction was carried out for 5 hours while maintaining the pH at 7.2 and the reaction temperature at 20° C.

The resulting reaction mixture was treated with a Bondapak $C_{18}$ column by the same method as in Example 5 to separate 2.0 mg of D-leucyl-L-phenylalanine methyl ester.

Elementary analysis of it ($C_{16}H_{24}N_2O_3$=292.36) was as follows: Calculation value (%): C: 65.73; H: 8.27; N: 9.58; Measured value (%): C: 65.62; H: 8.41; N: 9.52

EXAMPLE 10

To 35 ml of a 50 mM phosphoric acid buffer solution containing 5 g of β-alanylamide having pH 7.5, 100 mg of magnesium chloride, 2 mg of L-methionine, 100 units of pyrophosphatase (produced by Boehringer Mannheim Co.) and 0.01 mg of dithiothreitol were added to obtain a mixture solution. To the resulting mixture, 1 mg of methionyl-tRNA synthetase obtained in Reference Example 3 was added, and the volume thereof was adjusted to 40 ml while maintaining the pH of the mixture at 7.5. To the mixture, 100 mg of disodium deoxyadenosine triphosphate was added, and the reaction was carried out by the same method as in Example 9 while maintaining the pH at 7.5 to separate 2.4 mg of L-methionyl-β-alanylamide.

Elementary analysis of it ($C_8H_{17}N_3O_2S$=219.30) was as follows: Calculation value (%): C: 43.81; H: 7.82; N: 19.16; Measured value (%): C: 43.69; H: 7.73; N: 19.20

EXAMPLE 11

To 45 ml of a 20 mM HEPES buffer solution containing 8 g of L-phenylalanine ethyl ester having pH 7.1, 150 mg of magnesium chloride, 300 mg of disodium adenosine triphosphate, 2 mg of L-asparagic acid, 200 units of pyrophosphatase (produced by Boehringer Mannheim Co.) and 0.01 mg of dithiothreitol were added, and the resulting mixture was adjusted so as to have a pH of 7.1 and a volume of 50 ml. To the resulting mixture, 0.1 mg of aspartyl-tRNA synthetase obtained in Reference Example 4 was added and well blended, and the mixture was allowed to stand for one day while maintaining the pH at 7.1 and the reaction temperature at 30° C. to carry out the reaction. The resulting reaction solution was treated by the same method as in Example 5 to obtain 3.4 mg of L-aspartyl-L-phenylalanine ethyl ester.

EXAMPLES 12, 13 AND 14

To 45 ml of a 20 mM HEPES buffer solution containing 4 g of L-tyrosyl-t-butyl ester having pH 8.0, 300 mg of magnesium chloride, 350 mg of disodium adenosine triphosphate, 1 mg of L-alginine, 200 units of pyrophosphatase (Boehringer Mannheim Co.) and 0.01 mg of dithiothreitol were added, and the resulting mixture was adjusted so as to have a pH of 8.0 and a volume of 50 ml. To the resulting mixture, 0.4 mg of alginyl-tRNA synthetase obtained in Reference Example 5 was added and well blended. The mixture was treated by the same method as in Example 5 while maintaining the pH at 8.0 to obtain 0.5 mg of L-alginyl-L-tyrosine-t-butyl ester.

The reaction was carried out by the same method as in Example 12 using D-tyrosine t-butyl ester instead of L-tyrosine t-butyl ester (Example 13).

As the result, 0.4 mg of L-alginyl-D-tyrosine t-butyl ester was obtained.

Further, the reaction was carried out by the same method as in Example 12 using D-alginine 1 mg instead of L-alginine in Example 12 (Example 14).

As the result, 0.4 mg of D-alginyl-L-tyrosine t-butyl ester was obtained.

EXAMPLE 15

0.4 g of tyrosyl-tRNA synthetase obtained in Reference Example 1, 0.4 g of magnesium chloride, 0.1 g of disodium adenosine triphosphate, 1 mg of L-tyrosine, 200 units of pyrophosphatase (produced by Boehringer Mannheim Co.) and 0.01 mg of dithiothreitol were dissolved in 140 ml of a 20 mM HEPES buffer solution having pH 8.0, and the resulting mixture was reacted at 4° C. for 15 minutes to obtain a reaction mixture. To the resulting reaction mixture, 0.4 g (1/10 of the amount in Example 1) of L-phenylalanine methyl ester and 60 ml (30% by volume) of acetonitrile were added and well blended. The mixture was allowed to stand for one day while maintaining the reaction temperature at 30° C. to carry out the reaction.

200 ml of acetone was added to the resulting reaction solution. After precipitates were filtered out, the supernatant solution was concentrated to about 20 ml by an evaporator, and it was put in a μ Bondapak $C_{18}$ column (produced by Waters Co.) and treated with an aqueous solution of acetonitrile/50 mM potassium phosphate: 85/15 having pH 7 as a developing solution to separate 0.4 mg of L-tyrosyl-L-phenylalanine methyl ester.

Elementary analysis of it ($C_{19}H_{22}N_2O_4 = 342.39$) was as follows: Calculation value (%): C: 66.65; H: 6.48; N: 8.18; Measured value (%): C: 66.48; H: 6.52; N: 8.52

EXAMPLE 16

5 g of tyrosyl-tRNA synthetase used in Example 1, 450 mg of magnesium chloride, 300 mg of disodium adenosine triphosphate, 9 mg of L-tyrosine, 200 units of pyrophosphatase (produced by Boehringer Mannheim Co.) and 0.01 mg of dithiothreitol were dissolved in 20 ml of a 10 mM buffer solution having pH 8.5. After the mixture was reacted at 4° C. for 20 minutes, the reaction mixture was put in a G-75 column (produced by Pharmacia Co.), and elution was carried out with the same HEPES buffer solution as described above to collect 30 ml of fraction in voids, and the reaction mixture was isolated. To the isolated reaction mixture, 0.5 g (⅛ of the amount in Example 2) of D-leucine ethyl ester and 15 ml (42% by volume) of acetonitrile were added and well blended, and the mixture was allowed to react for 30 minutes while maintaining the reaction temperature at 20° C.

The resulting reaction solution was put in a Bondapak $C_{18}$ column, and separation was carried out by the same method as in Example 1 to obtain 15 mg of L-tyrosyl-D-leucine ethyl ester.

Elementary analysis of it ($C_{17}H_{26}N_2O_4 = 322.39$) was as follows: Calculation value (%): C: 63.33; H: 8.13; N: 8.69; Measured value (%): C: 63.30; H: 8.08; N: 8.75

EXAMPLES 17 AND 18

20 mg of tyrosyl-tRNA synthetase prepared from baker's yeast according to the method described in Example 3, 50 mg of magnesium chloride, 20 mg of disodium adenosine triphosphate, 0.1 mg of D-tyrosine, 10 units of pyrophosphatase (produced by Boehringer Mannheim Co.) and 20 μl of mercaptoethanol were added to 20 ml of a 30 mM 2,5-dimethylimidazole buffer solution having pH 9. After reacting by the same method as in Example 16, the reaction mixture was isolated. To the reaction mixture, 0.1 g (1/10 of the amount in Example 3) of L-leucine ethyl ester and 10 ml (25% by volume) of acetonitrile were added to carry out the reaction at 20° C. for 5 hours. 20 ml of acetone was added to the resulting reaction product and formed precipitates were filtered out. After being concentrated to about 10 ml by an evaporator, separation was carried out by the same method as in Example 1 to obtain D-tyrosyl-L-leucine ethyl ester (Example 17).

The same procedure as described above was carried out while adding 15 ml of dimethyl sulfoxide instead of 10 ml of acetonitrile (Example 18).

As a result, the yield of D-tyrosyl-L-leucine ethyl ester was as follows:

|  | Yield (mg) |
| --- | --- |
| Example 17 | 0.16 |
| Example 18 | 0.15 |

EXAMPLE 19

6 kg of *Bacillus stearothermophilus* was suspended in 12 liters of a 100 mM tris-hydrochloric acid buffer solution (pH 7.5). After cells were crushed by a Dynomill, insoluble materials were removed by centrifugal separation to obtain a crude extract solution containing tyrosyl-tRNA synthetase having specificity to tyrosine. The above described crude extract solution was allowed to pass through a column packed with cellulose phosphate (produced by Whatman Co.) which was previously equilibrated with a 50 mM phosphoric acid buffer solution (pH 7.0) containing 5 mM mercaptoethanol, 2 mM sodium ethylenediaminetetraacetate and 0.1 mM phosphophenylsulfonyl fluoride. When elution was carried out at a linear velocity of 60 cm.hr with a solution prepared by adding potassium chloride to the above descibed buffer solution, tyrosyl-tRNA synthetase was eluted. This fraction was collected and concentration and desalting were carried out, by which a crude enzyme solution containing tyrosyl-tRNA synthetase having specificity to tyrosine was obtained in a high yield of 80% or more. The above described operations were all carried out at 4° C.

30 g of the crude enzyme solution containing tyrosyl-tRNA synthetase obtained by treating with the phosphoric acid group containing cation exchange resin as described above (purity 1%), 0.4 g of magnesium chloride, 0.1 g of disodium adenosine triphosphate, 1 mg of L-tyrosine, 200 units of pyrophosphatase (produced by Boehringer Mannheim Co.) and 0.01 mg of dithiothreitol were dissolved in 200 ml of a 20 mM HEPES buffer solution having pH 8.0, and the mixture was blended at 4° C. for 15 minutes. To the resulting mixture, 4 g of L-alanine methyl ester was added and well blended, and the resulting mixture was allowed to stand for one day while maintaining the reaction temperature at 30° C. to carry out the reaction.

200 ml of acetone was added to the resulting reaction solution. After precipitates were filtered out, the supernatant solution was concentrated to about 20 ml by an evaporator, and it was put in a Bondapak $C_{18}$ column (produced by Waters Co.) and treated with an aqueous solution of acetonitrile/50 mM potassium phosphate: 85/15 having pH 7 as a developing solution to separate 0.4 mg of L-tyrosyl-L-phenylalanine methyl ester.

Elementary analysis of it ($C_{19}H_{22}N_2O_4 = 342.39$) was as follows: Calculation value (%): C: 66.65; H: 6.48; N: 8.18; Measured value (%): C: 66.71; H: 6.37; N: 8.23

EXAMPLE 20

A crude extract solution obtained by the same method as in Example 1 using 55 kg of *Bacillus stearothermophilus* was added to phosphoric acid Celex (produced by Bio-Rád Co.) which was previously equilibrated with a 20 mM phosphoric acid buffer solution (pH 7.5) containing 5 mM mercaptoethanol, 2 mM sodium ethylenediaminetetraacetate and 0.1 mM phosphophenylsulfonyl fluoride, and the mixture was stirred for 30 minutes. After being allowed to stand for a few minutes, the supernatant was removed, and elution was carried out with a solution obtained by adding sodium chloride to the above described buffer solution, by which tyrosyl-tRNA synthetase was eluted. The above described operations were all carried out at 30° C.

27 g of the crude enzyme solution containing tyrosyl-tRNA synthetase obtained by treating with the phosphoric acid group containing cation exchange resin (purity 1%), 450 mg of magnesium chloride, 300 mg of disodium adenosine triphosphate, 9 mg of L-tyrosine, 200 units of pyrophosphatase (produced by Boehringer Mannheim Co.) and 0.01 mg of dithiothreitol were dissolved in 200 ml of a 25 mM phosphoric acid buffer solution having pH 8.5. After the reaction was carried out at 4° C. for 20 minutes, the reaction mixture was put in a G-75 column (produced by Pharmacia Co.) and elution was carried out with a HEPES buffer solution to collect 300 ml of the fraction in voids, by which the reaction mixture was isolated. To the isolated mixture, 1.0 g of D-valine methyl ester was added and well blended, and the reaction was carried out for 30 minutes while maintaining the reaction temperature at 20° C.

The resulting reaction solution was then added to 1 liter of acetone. After precipitates were filtered out, the supernatant solution was concentrated to about 30 ml by an evaporator, and it was put in a $\mu$ Bondapak $C_{18}$ column. Separation was carried out by the same method as in Example 1 to obtain 14.6 mg of L-tyrosyl-D-valine methyl ester.

Elementary analysis of it ($C_{15}H_{22}N_2O_4 = 294.36$) was as follows: Calculation value (%): C: 61.21; H: 7.53; N: 9.52; Measured value (%): C: 61.41; H: 7.50; N: 9.39

EXAMPLES 21 AND 22

A crude extract solution obtained from baker's yeast by the same procedure as in Example 19 was allowed to pass through a column packed with cellulose phosphate (produced by Serva Co.) which was previously equilibrated with a 50 mM phosphoric acid buffer solution (pH 7.0) containing 10 mM mercaptoethanol, 20 mM sodium ethylenediaminetetraacetate and 0.1 mM phosphophenylsulfonyl fluoride. When elution was carried out at a linear velocity of 10 cm.h$^{-1}$ with a solution prepared by adding potassium chloride to the above described buffer solution, a crude enzyme solution containing methionyl-tRNA synthetase was eluted. It was freeze-dried to obtain a powdery enzyme sample.

2 g of the crude enzyme sample containing methionyl-tRNA synthetase obtained by treating with the phosphoric acid group containing cation exchange resin (purity 10%), 50 mg of magnesium chloride, 40 mg of disodium adenosine triphosphate, 1 mg of D-methionine, 10 units of pyrophosphatase (produced by Boehringer Mannheim Co.) and 20 $\mu$l of mercaptoethanol were added to 30 ml of a 50 mM 2,5-dimethylimidazole buffer solution having pH 9.0. After reacting by the same method as in Example 20, the reaction mixture was isolated by the same method as in Example 2. 1 g of L-leucine ethyl ester was added in a solid state to the resulting reaction mixture to carry out the reaction at 20° C. for 5 hours. 20 ml of acetone was added to the resulting reaction product, and formed precipitates were filtered out. After being concentrated to about 10 ml by an evaporator, separation was carried out by the same method as in Example 1 to obtain 1.8 mg of D-methionyl-L-leucine ethyl ester (Example 21).

Elementary analysis of it ($C_{13}H_{26}N_2O_3S_1 = 290.43$) was as follows: Calculation value (%): C: 53.77; H: 9.02; N: 9.64; Measured value (%): C: 53.80; H: 8.90; N: 9.75

Further, using the crude extract solution obtained as described above without treating with the phosphoric acid group containing cation exchange resin, the reaction was carried out by the same method as described above to obtain 0.2 mg of D-methionyl-L-leucine ethyl ester (Example 22).

The yield had a tendency to decrease, as compared with Example 21, because of side reactions caused by the influence of other enzymes present in the crude extract solution.

EXAMPLES 23 AND 24

A crude extract solution containing seryl-tRNA synthetase was obtained from rabbit liver by the same procedure as in Example 1 using a homogenizer. This crude extract solution was added to cellulose phosphate (produced by Whatman Co.) which was previously equilibrated with a 25 mM imidazole buffer solution (pH 7.5) containing 1 mM dithiothreitol, 2 mM sodium ethylenediaminetetraacetate and 0.1 mM phosphophenylsulfonyl fluoride, and the mixture was stirred for one hour. After being allowed to stand, the supernatant was removed. When elution was carried out with a solution prepared by adding potassium chloride to the above described buffer solution, seryl-tRNA synthetase was eluted.

Using 3 g of the resulting crude enzyme solution containing seryl-tRNA synthetase (purity 10%), 50 mg of magnesium chloride, 50 mg of disodium deoxyadenosine triphosphate, 1 mg of L-serine, 200 units of pyrophosphatase (produced by Boehringer Mannheim Co.) and 0.01 mg of dithiothreitol, the reaction was carried out by the same method as in Example 3, and a reaction mixture was obtained using a G-25 column (produced by Pharmacia Co.). Then, 4 g of $\beta$-alanylamide was added thereto and blended to carry out the reaction at 50° C. for 10 minutes. The resulting reaction solution was treated with a $\mu$ Bondapak $C_{18}$ column by the same method as in Example to separate 1.3 mg of L-seryl-$\beta$-alanylamide (Example 23).

Elementary analysis of it ($C_6H_{13}N_3O_3 = 175.19$) was as follows: Calculation value (%): C: 41.14; H: 7.48; N: 23.99; Measured value (%): C: 41.10; H: 7.43; N: 24.05

Further, using the crude extract solution obtained as described above without treating with the phosphoric acid group-containing cation exchange resin, the reaction was carried out by the same method as described above to obtain 0.2 mg of L-seryl-$\beta$-alanylamide (Example 24).

From the above examples, it can be seen that when the crude enzyme solution containing seryl-tRNA synthetase obtained by treating with the phosphoric acid group-containing cation exchange resin, the yield of the L-seryl-$\beta$-alanylamide is increased and it is produced at a moderate price, whereas when the crude extract solution obtained without treating with the phosphoric acid group-containing cation exchange resin, it tends to show a low yield of the L-seryl-$\beta$-alanylamide.

While the invention has been described in detail and with reference to specific embodiments thereof, it will be apparent to one skilled in the art that various changes and modifications can be made therein without departing from the spirit and scope thereof.

What is claimed is:

1. A process for synthesizing a peptide or a peptide derivative thereof comprising enzymatically bonding (a) a first amino acid to (b) a second amino acid, which may be the same or different than the first amino acid, or an amino acid derivative having a full amino group, with a condensing agent, wherein said condensing agent is aminoacyl-tRNA synthetase.

2. A process for synthesizing a peptide or a peptide derivative thereof according to claim 1, wherein the first amino acid is enzymatically bound to an amino acid derivative having a full amino group.

3. A process for synthesizing a peptide or a peptide derivative thereof as claimed in claim 2, which comprises previously reacting the first amino acid with aminoacyl-tRNA synthetase and reacting the resulting reaction mixture with an amino acid derivative having a full amino group.

4. A process for synthesizing a peptide or a peptide derivative thereof as claimed in claim 3, which comprises the steps of: (1) admixing an amino acid, an aminoacyl-tRNA synthetase and a triphosphate selected from the group consisting of adenosine triphosphate and deoxyadenosine triphosphate in the presence of a buffer solution to obtain a reaction mixture; (2) adding the reaction mixture to an amino acid derivative having a full amino group; (3) reacting the resulting reaction mixture so as to form a peptide or a peptide derivative thereof; and (4) removing the resulting peptide or peptide derivative thereof from the reaction system.

5. A process for synthesizing a peptide or a peptide derivative thereof as claimed in claim 1, which comprises previously admixing the first amino acid with the second amino acid or an amino acid derivative having a full amino group, and reacting the resulting reaction mixture with an aminoacyl-tRNA synthetase.

6. A process for synthesizing a peptide or a peptide derivative thereof as claimed in claim 5, which comprises the steps of: (1) admixing the first amino acid with the second amino acid, or an amino acid derivative having a full amino group and a triphosphate selected from the group consisting of adenosine triphosphate and deoxyadenosine triphosphate in the presence of a buffer solution to obtain a reaction mixture; (2) adding the reaction mixture to an aminoacyl-tRNA synthetase; (3) reacting the resulting reaction mixture so as to form a peptide or a peptide derivative thereof; and (4) removing the resulting peptide or peptide derivative thereof from the reaction system.

7. A process for synthesizing a peptide or a peptide derivative thereof as claimed in claim 1, which comprises previously admixing the second amino acid or an amino acid derivative having a full amino group with aminoacyl-tRNA synthetase, and reacting the resulting reaction mixture with the first amino acid.

8. A process for synthesizing a peptide or a peptide derivative thereof as claimed in claim 7, which comprises the steps of: (1) admixing an amino acid derivative having a free amino group or the second amino acid with an aminoacyl-tRNA synthetase and a triphosphate selected from the group consisting of adenosine triphosphate and deoxyadenosine triphosphate in the presence of a buffer solution to obtain a reaction mixture; (2) adding the reaction mixture to the first amino acid; (3) reacting the resulting reaction mixture so as to form a peptide or a peptide derivative thereof; and (4) removing the resulting peptide or peptide derivative thereof from the reaction system.

9. A process for synthesizing a peptide or a peptide derivative thereof as claimed in claim 1, wherein said aminoacyl-tRNA synthetase is in the form of a crude enzyme solution containing said aminoacyl-tRNA synthetase, wherein said crude enzyme solution is obtained by crushing cells to obtain a crude extract solution and then adding the crude extract to a cation exchange resin having phosphoric groups and eluting said aminoacyl-tRNA synthetase.

10. A process for synthesizing a peptide or a peptide derivative thereof as claimed in claim 1 wherein a hydrophilic organic solvent is present in the reaction system.

11. A process for synthesizing a peptide or a peptide derivative thereof as claimed in claim 4, wherein the buffer solution has a pH within the range of 7 to 10.

12. A process for synthesizing a peptide or a peptide derivative thereof as claimed in claim 4, wherein the reaction mixture is blended at a temperature within the range of 0° C. to 30° C.

13. A process for synthesizing a peptide or a peptide derivative thereof as claimed in claim 4, wherein the reaction is carried out in the presence of a hydrophilic organic solvent present in a concentration of 10 to 50%.

14. A process for synthesizing a peptide or a peptide derivative thereof as claimed in claim 4, wherein the molar ratio of the amino acid to the aminoacyl-tRNA synthetase is within the range of 1:1 to 1:10.

15. A process for synthesizing a peptide or a peptide derivative thereof as claimed in claim 4, wherein the molar ratio of the amino acid to the triphosphate is within the range of 1:10 to 1:100.

16. A process for synthesizing a peptide or a peptide derivative thereof as claimed in claim 4, wherein the reaction is carried out at a temperature within the range of 20° C. to 40° C. at a pH within the range of 7 to 9.

17. A process for synthesizing a peptide or a peptide derivative thereof as claimed in claim 4, wherein the reaction mixture and amino acid derivative are added together in a ratio by volume within the range of 1:0.1 to 1:100.

18. A process for synthesizing a peptide or a peptide derivative thereof as claimed in claim 10 wherein the hydrophilic organic solvent is selected from the group consisting of dioxane, tetrahydrofuran, dimethylsulfoxide, dimethylformamide, acetonitrile and acetone.

19. A process for synthesizing a peptide or a peptide derivative thereof as claimed in claim 13 wherein the hydrophilic organic solvent is selected from the group consisting of dioxane, tetrahydrofuran, dimethylsulfoxide, dimethylformamide, acetonitrile and acetone.

20. A process for synthesizing a peptide or a peptide derivative as claimed in claim 1, wherein said process is carried out at a pH range of 5 to 11 and a temperature of 0° to 70° C.

21. A process for synthesizing a peptide or a peptide derivative thereof according to claim 20, wherein said pH is 6 to 10.

22. A process for synthesizing a peptide or a peptide derivative thereof according to claim 21, wherein said pH is 7 to 10.

23. A process for synthesizing a peptide or a peptide derivative thereof as claimed in claim 20, wherein said temperature is 0° C. to 30° C.

* * * * *